United States Patent [19]

Cox et al.

[11] 4,111,194

[45] Sep. 5, 1978

[54] POSTERIOR KNEE IMMOBILIZING BRACE

[76] Inventors: Rollin Webb Cox, 340 Bimini Dr., Merritt Island, Fla. 32952; Randy Charles Watson, 2201 South St., South Lake Tahoe, Calif. 95731

[21] Appl. No.: 754,004

[22] Filed: Dec. 27, 1976

[51] Int. Cl.$^2$ ............................................. A61F 3/00
[52] U.S. Cl. .................................................. 128/80 C
[58] Field of Search ................... 128/80 C, 80 R, 87, 128/165; 2/22, 24

[56] References Cited

U.S. PATENT DOCUMENTS

| | | | |
|---|---|---|---|
| 3,463,147 | 8/1969 | Stubbs | 128/165 X |
| 3,831,467 | 8/1974 | Moore | 128/80 C |
| 3,853,123 | 12/1974 | Moore | 128/80 C |
| 3,911,497 | 10/1975 | Lewis, Jr. et al. | 128/165 X |

Primary Examiner—John D. Yasko

[57] ABSTRACT

A temporary knee immobilizing brace or splint comprising a preformed plastic shell covering the posterior portion of the leg and knee joint with circumferential straps formed as part of the shell. Strap sections are padded internally of the shell to form non-slip garter type fastenings. The shell is relieved in the area of the knee joint to prevent contact in the area of the peroneal nerve. Positioning padding is provided along the posterior length of the interior of the shell and a positioning wedge of padding is provided at the popliteal region of the joint insuring joint flexure and minimal contact between the skin and shell of the brace, thereby allowing breathing of the skin and ease of exterior examination. A separate shield which protects the patella from injury is additionally provided.

9 Claims, 6 Drawing Figures

POSTERIOR KNEE IMMOBILIZING BRACE

BACKGROUND OF THE INVENTION

Injuries to the knee joint requiring various periods of immobilization are both painful and common due especially to various rigorous sports such as football and skiing, as well as resulting from other misadventures or organic causes.

The means for immobilizing the knee joint by other than plaster casting or other semi-permanent procedures are subject to numerous deficiencies which cause unnecessary discomfort to the patient as well as contributing to further disabling conditions unrelated to the injury being treated.

Pressure by temporary splints on the area of the knee where the peroneal nerve passes close to the surface causes both pain and involuntary reflex or spasm reactions and contributes both to patient discomfort and extended convalescence of the joint.

Contact between the skin and brace or splint apparatus over large surface areas and extended time periods causes extensive sweating, dirt buildup, abrasion and resultant skin maceration.

Slipping or shifting of the appliance when in use causes discomfort and requires constant refitting of the appliance by the patient, which disturbance of the joint may lead to further extended recovery periods.

Braces in common use require removal for external inspection of the affected leg or for purposes of X-ray, since they cover substantially the entire surrounding area and contain various X-ray opaque parts or stiffeners.

SUMMARY OF THE INVENTION

The above disadvantages and others are overcome by use of the knee immobilizing brace of the present invention which generally comprises a preformed shell shaped to support the posterior portion of the leg on either side of the knee joint with preformed strap sections of the shell extending around the front of the leg. A pad runs the length of the shell supporting the leg away from contact with the shell and a further wedge-shaped pad engages the rear of the knee joint. Bands of padded material extend around the shell and strap portions forming garter-like closures which prevent slipping of the brace. The shell is relieved in the region of the knee joint to prevent contact with the joint in the region of the peroneal nerve. A more heavily padded strap portion covers the bony frontal area where the lower strap passes over the tibia, and a protective cover may be used when it is desired to protect the patella from contact with foreign objects.

BRIEF DESCRIPTION OF THE DRAWINGS

Further embodiments of this invention will become evident upon study of the detailed description and drawings which follow in which.

DESCRIPTION OF THE PREFERRED EMBODIMENTS

Figure 1:
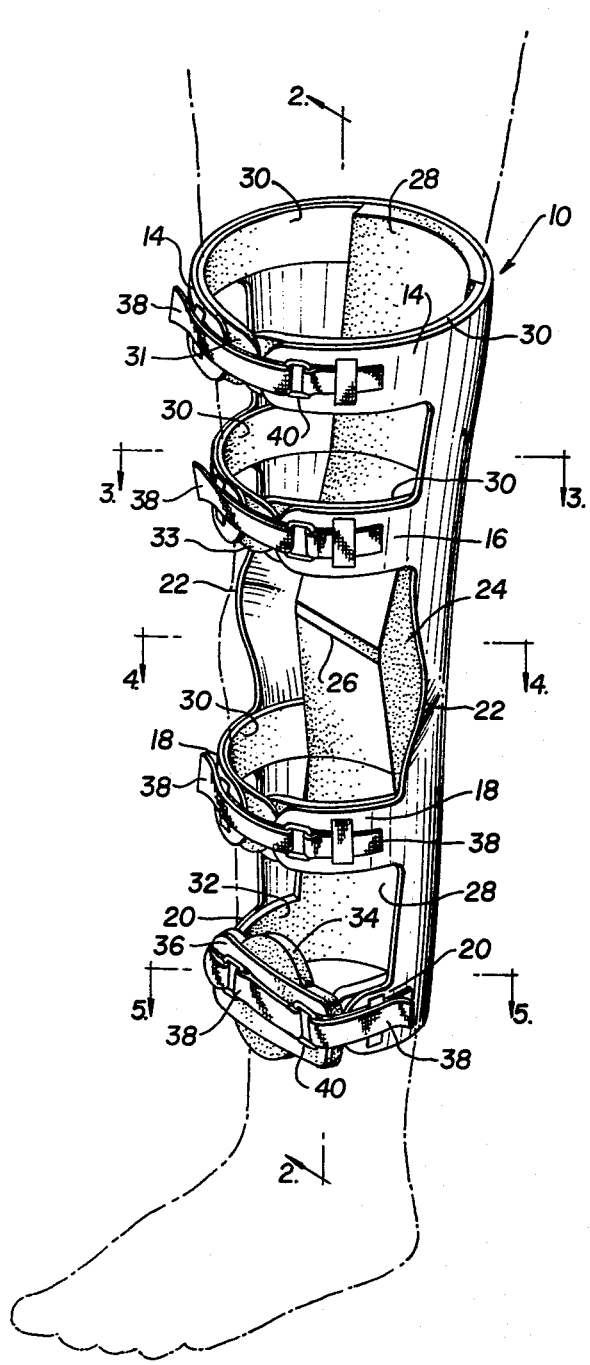
FIG. 1 is a front perspective view of the brace of the present invention in place on a typical leg.

The brace of the present invention generally comprises a shell 10 preferably a unitary piece of plastic or other suitable material molded or shaped to the general contours of the posterior half of a leg on either side of the knee joint. The shell 10 may be originally cut from a sheet of suitable material such as high density polyethelene and, when flat, comprises a generally trapezoidal central section and pairs of elongated opposed strap sections 14, 16, 18 and 20. The strap sections 14, 16, 18 and 20 preferably are formed integrally with the shell 10 to form generally matching strap sections substantially following the contours of a leg, as illustrated in FIG. 1.

Figure 2:
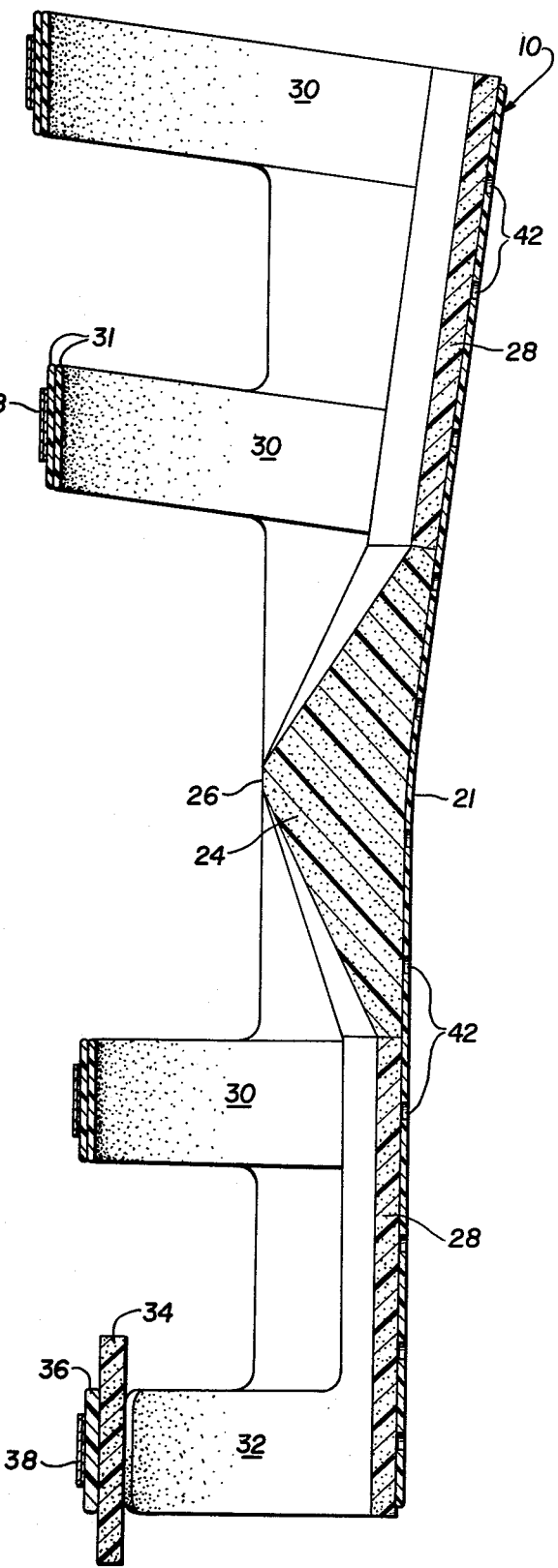
FIG. 2 is a sectional view taken substantially along line 2—2 of FIG. 1.
Figure 3:
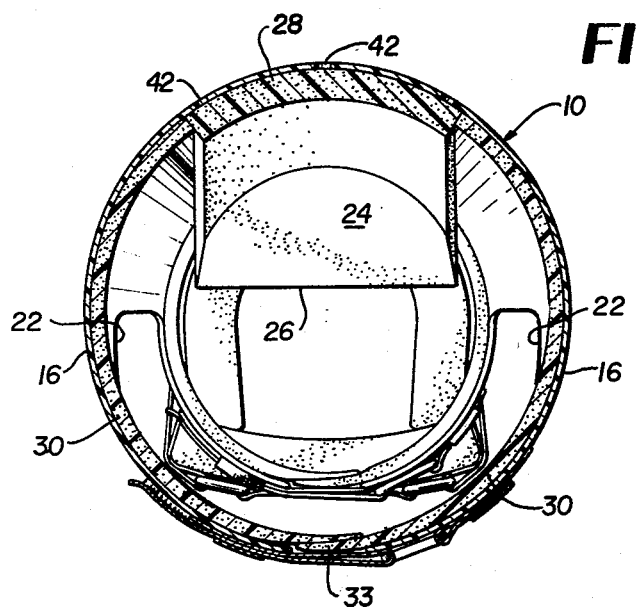
FIG. 3 is a sectional view taken substantially along line 3—3 of FIG. 1.

The shell 10 is formed to provide a generally semicircular cross section of the same general tapered shape as a normal leg and is of a slightly larger circumferential dimension along the interior surface than the leg to which it is to be applied. A slight bend 21 preferably is formed in the shell 10, as shown in FIG. 2, to hold the limb in a relaxed position.

Figure 4:
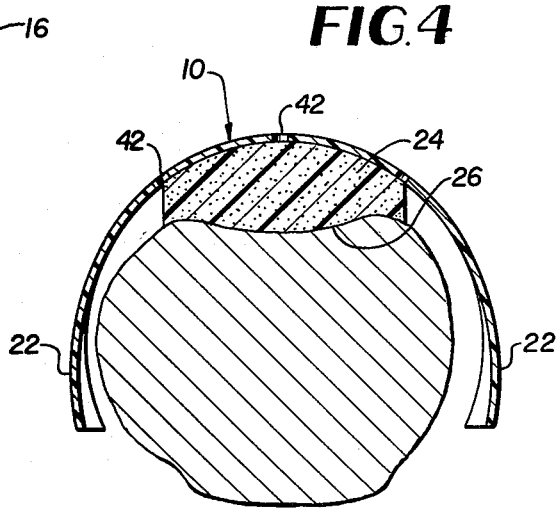
FIG. 4 is a sectional view taken substantially along line 4—4 of FIG. 1, illustrating the positioning of a knee joint.
Figure 5:
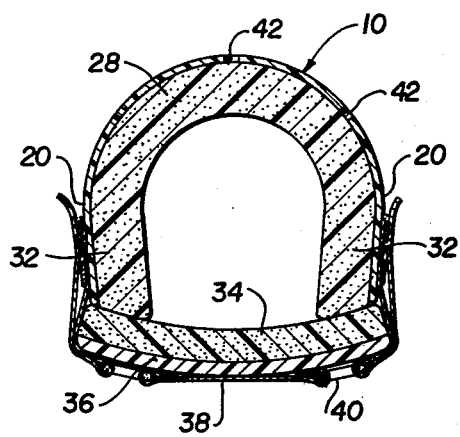
FIG. 5 is a sectional view taken substantially along line 5—5 of FIG. 1.

Relief from the generally regular taper of the cross section is provided at 22 in the region accepting the knee joint. This relieved section 22 preferably is of sufficient size that no contact is made between the completed apparatus and the knee joint, as illustrated in FIG. 4, except at the extreme posterior or popliteal region of the joint.

A wedge member 24, preferably formed of soft open cell foam or another suitable material is affixed by a suitable adhesive or other suitable means to the interior of the shell 10 in a position which places the apex 26 of the wedge member 24 in the popliteal region behind the knee joint. The wedge member 24 preferably has a flattened apex 26 as shown in FIG. 1 or, alternatively, may be rounded. The wedge member 24 preferably is of sufficient thickness at the apex 26 to ensure slight flexure of the knee joint when the appliance is in use and provide substantially continuous contact with the irregularly shaped popliteal region of the rear of the knee joint.

A posterior pad 28 preferably made from soft open cell foam or another material similar to that of the wedge member 24 extends from either end of the wedge 24 along the posterior portion of the shell 10 and terminates slightly beyond the ends of the shell 10. The posterior pad 28 need be only of a thickness and width to comfortably support the leg and to substantially prevent contact between the skin of the leg and the interior of the shell 10. The posterior pad 28 may be made as part of the wedge member 24 or in separate sections as shown in FIG. 2.

Padded bands 30 extend around the interior of the shell 10 from the posterior pad 28, along and to the ends of the strap sections 14, 16 and 18. The padded bands 30 preferably are formed from a high density open cell foam or another suitable material and preferably are slightly wider than the straps 14, 16, 18 and terminate beyond the ends of the respective straps in tapered rounded ends 31.

Extensions 32 of the posterior pad 28 or separate pieces of similar material extend from the posterior pad 28 along the path of the strap sections 20 slightly wider than the strap sections 20 and terminating slightly beyond the ends thereof.

The strap sections 20 may extend long enough to substantially surround the corresponding leg section but preferably are reduced from this length and extend to a distance from the posterior line of the shell 10 less than the thickness of the leg at the corresponding point. A separate pad 34 preferably wider than the strap sections 20 and preferably made from a soft open cell foam material with a backing strip 36 of a more dense material extends between the ends of the strap sections 20 to form a closure at this location.

Bindings between the strap sections 14, 16, 18 and 20, and across the pad 34 preferably are adjustable straps 38 made from VELCRO material or other suitable material, and are attached to their respective strap sections 14, 16, 18, 20 and the pad 36 by adhesive or any other suitable means. Loops 40 or other suitable fittings may be used to reduce the unit loading on the straps 38 if desired. The loops 40 as well as other parts of the appliance preferably are made from materials that are substantially X-ray transparent, lightweight and non-irritating to the skin.

Ventilating holes 42 preferably are provided at uniform intervals in the shell 10 under the region covered by the posterior pad 28 and wedge member 24.

In the use of the brace of the present invention, a shell 10 is chosen from a variety of sizes corresponding to the leg to which it is to be applied. The strap sections 14, 16 and 18 are held open and the leg is positioned within the shell 10. The straps 38 are threaded through their respective loops 40 and tightened sufficiently to bring the padded bands 30 and 32 in substantially continuous contact with the leg. The wedge member 24 provides comfortable yet firm support for the popliteal region. The posterior pad 28 and padded bands 30 and 32 firmly position the leg within the shell 10 and prevent undesirable bending either laterally or in flexion.

The padded bands 30 in contact with the leg surface provide a garter effect and, in cooperation with the wedge member 24, effectively prevent shifting or slipping of the appliance. The tapered ends 31 of the padded bands 30 preferably overlap their opposite member resulting in a continuous band around the circumference of the leg. Skin contact is limited to the padded areas underlying the straps 14, 16, 18 and 20, the pad 34, the wedge member 24 and the posterior pad 18. These contact areas, being formed from open cell foam material allow breathing of the skin surface limiting the sweating and resultant skin irritation commonly experienced with restrictive appliances. The remaining majority of the skin area on the leg is held away from contact with the shell 10 to further reduce the potential for irritation.

The open structure of the shell 10 allows exterior examination and cleansing of the leg and joint without removal of the appliance or disturbance of the joint being immobilized. X-ray examination of the leg may be made with the appliance in place since all preferred materials of construction are substantially X-ray transparent.

The pad 32 spreads the fastening load along the bony prominance of the tibia that is covered, effectively limiting pressure points and potential irritation at this location.

The ventilating holes 42 provide further relief from stagnation of air circulation in the region of the posterior pad 28 and wedge member 24, relieving potential discomfort in this region.

The relieved areas 22 of the shell 10 effectively prevent external contact with the area of the peroneal nerve relieving potential discomfort from this very common occurrence.

Figure 6:
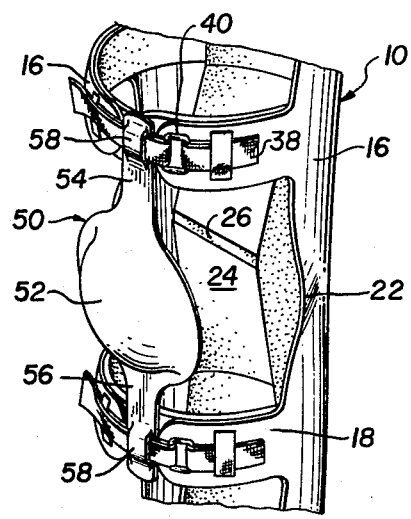
FIG. 6 is a partial front perspective view illustrating a protective shield for the patella in place.

In instances where external contact with the patella is desirable, a second embodiment is provided comprising the appliance already described in combination with an auxillary patella protector 50. As illustrated in FIG. 6, the patella protector 50 is preferably made from a single preformed piece of generally rigid sheet material similar to the material of the shell 10.

The patella protector 50 comprises a dome-shaped central portion 52 covering the patella region of the knee and held out of contact with the patella by two tongues 54 and 56 extending between and supported by the strap sections 16 and 18. Strap guides 58 or similar fastening means are provided in the tongues 54 and 56 in a conventional manner. The fastening straps 38 on strap sections 16 and 18 pass through the strap guides 58 to secure the patella protector 50 in the desired location without affecting the fit or function of the knee immobilizing brace itself.

The patella protector in combination with the knee immobilizing brace is of particular utility in instances of knee or cartilage surgery where immobilization of the knee and protection of the patella region is of prime importance in therapy, but casting is undesirable owing to requirements for dressing changes and/or periodic exercise treatments.

What is claimed is:

1. A knee brace comprising:
an elongated shell of generally semi-circular cross section having an elongated front opening of a width sufficient to enable a knee and adjacent leg portions to be positioned within said shell, said shell comprising a plurality of longitudinally spaced pairs of opposed flexible strap sections extending laterally into said front opening, said strap sections being movable between an open position wherein a leg may be positioned in or removed from said shell through said front opening and a closed position wherein the strap sections of each pair are disposed in closely spaced relation across said front opening and serve to retain a leg in said shell,
air permeable padding means disposed on the inner surface of said shell and extending longitudinally along the rear portion thereof and from the rear portion thereof along the inner surface of said strap sections, said padding means comprising an inwardly extending wedge member having the apex thereof located such that it will be adjacent to the popliteal region behind the knee joint of a leg positioned in said shell, and
means for releasably retaining said strap sections in said closed position,
said shell being provided with outwardly relieved portions on both sides thereof adjacent to the apex of said wedge member to insure against contact between the shell and the knee joint of a leg positioned therein at said portions.

2. The brace of claim 1 wherein said shell is formed of a plastic material, and said padding means is formed of an open cell foam material.

3. The brace of claim 1 wherein said shell is tapered downwardly and inwardly in a manner similar to a leg to be positioned therein.

4. The brace of claim 1 wherein said padding means extends beyond the ends of said shell and said strap sections.

5. The brace of claim 1 wherein the padding means extending beyond the ends of some of the opposing strap sections is overlapped.

6. The brace of claim 1 wherein a pad is disposed between and connected to the ends of the lowermost pair of strap sections, said pad being wider than the adjacent strap sections.

7. The brace of claim 1 wherein protecting means adapted to cover the patella portion of a knee is mounted on said shell between adjacent pairs of said strap sections.

8. The brace of claim 1 wherein said retaining means comprises straps connected to said strap sections, and means for releasably locking opposing straps together.

9. The brace of claim 1 wherein said shell is provided with a plurality of ventilating holes through the rear portion thereof.

* * * * *